United States Patent [19]

Nair et al.

[11] 4,066,829

[45] Jan. 3, 1978

[54] MALTO-DEXTRIN POLY(H-)SULFATES

[75] Inventors: Vijay Gopalan Nair, Nanuet, N.Y.; Joseph Peter Joseph, Cliffside Park, N.J.; Seymour Bernstein, New City, N.Y.

[73] Assignee: American Cyanamid Company, Stamford, Conn.

[21] Appl. No.: 704,583

[22] Filed: July 12, 1976

[51] Int. Cl.$^2$ ................................................ C13L 1/10
[52] U.S. Cl. ..................................... 536/103; 424/180; 536/46; 536/112; 536/118
[58] Field of Search ...................... 536/1, 46, 103, 118, 536/112; 424/180

[56] References Cited

U.S. PATENT DOCUMENTS

| | | | |
|---|---|---|---|
| 2,686,779 | 8/1954 | Jones | 536/103 |
| 2,697,093 | 12/1954 | Jones | 536/103 |
| 3,017,407 | 1/1962 | Petracek et al. | 536/103 |
| 3,070,595 | 12/1962 | Petracek et al. | 536/118 |

*Primary Examiner*—Johnnie R. Brown
*Attorney, Agent, or Firm*—Jack W. Richards

[57] ABSTRACT

Malto-dextrin poly(H-)sulfate and salts thereof useful as inhibitors of the complement system.

12 Claims, No Drawings

MALTO-DEXTRIN POLY(H-)SULFATES

BACKGROUND OF THE INVENTION

The present invention is directed to a process for producing malto-dextrin poly(H-)sulfate and salts thereof, with the malto-dextrin poly(H-)sulfates so produced and with their utility as inhibitors of the complement system of warm-blooded animals.

Sulfation products of maltose, lactose, sucrose, manninotriose and stachyose are known, *J. Pharm. Soc. Japan*, 87: 1052 (1967). *British J. Pharmacol.*, 7: 370 (1952) discloses sulfuric acid esters of starch and *Acta Physiologica Scand.*, 8:215 (1944); 9: 28 (1945); 9 : 35 (1945); and 11 : 211 (1946), sulfuric acid esters of starch having anticoagulant and platelet agglutination activity. Certain sulfated polysaccaharides are disclosed as having anti-inflammatory action, e.g., dextran sulfate, pentosan polysulfate and amylopectin sulfate, *Biochemical Pharmacology*, 18:1285 (1969). Japanese Pat. No. 75/36422 (*Chemical Abstracts*, 83: 79544a) discloses cyclodextrin sulfates as anti-inflammatory, fatty serum clarifiers and arteriosclerotic agents. Sulfuric esters of maltose oligosaccharides have been investigated for anticoagulant activity, *Chemistry and Industry*, October, 1952, 982. Dextrin sulfate has been shown to possess anticoagulant acitivity, *Fed. Proc.*, 9:188 (1950). The sulphated polysaccaharide heparin is known to have anticomplementary activity, e.g., *J. Infect. Dis.*, 44 : 250 (1929). Pentosan polysulfo ester and dextran sulfate are also said to posses anti-complementary action, *Chemical Abstracts*, 52: 485h (1958) and 75:33179s (1971).

The term "complement" refers to a complex group of proteins in body fluids that, working together with antibodies or other factors, play an important role as mediators of immune, allergic, immunochemical and/or immunopathological reactions. The reactions in which complement participates takes place in blood serum or in other body fluids, and hence are considered to be humoral reactions.

With regard to human blood, there are at present more than 11 proteins in the complement system. These complement proteins are designated by the letter C and by number: C1, C2, C3 and so on up to C9. The complement protein C1 is actually an assembly of subunits designated C1q, C1r and C1s. The numbers assigned to the complement proteins reflect the sequence in which they become active, with the exception of complement protein C4, which reacts after C1 and before C2. The numerical assignments for the proteins in the complement system were made before the reaction sequence was fully understood. A more detailed discussion of the complement system and its role in body processes can be found in, for example, *Bull. World Health Org.*, 39, 935-938 (1968); *Scientific American*, 229, (No. 5), 54-66 (1973); *Medical World News*, Oct. 11, 1974, pp. 53-58; 64-66; *Harvey Lectures*, 66, 75-104 (1972); *The New England Journal of Medicine*, 287, 489-495; 545-549; 592-596; 642-646 (1972); *The Johns Hopkins Med. J.*, 128, 57-74 (1971); and *Federation Proceedings*, 32, 134-137 (1973).

The complement system can be considered to consist of three sub-systems: (1) a recognition unit (C1q) which enables it to combine with antibody molecules that have detected a foreign invader; (2) an activation unit (C1r, C1s, C2, C4, C3), which prepares a site on the neighboring membrane; and (3) an attack unit (C5, C6, C7, C8 and C9) which creates a "hole" in the membrane. The membrane attack unit is non-specific; it destroys invaders only because it is generated in their neighborhood. In order to minimize damage to the host's own cells, its activity must be limited in time. This limitation is accomplished partly by the spontaneous decay of activated complement and partly by interference by inhibitors and destructive enzymes. The control of complement, however, is not perfect, and there are times when damage is done to the host's cells. Immunity is therefore a double-edged sword.

Activation of the complement system also accelerates blood clotting. This action comes about by way of the complement-mediated release of a clotting factor from platelets. The biologically active complement fragments and complexes cn become involved in reactions that damage the host's cells, and these pathogenic reactions can result in the development of immune-complex diseases. For example, in some forms of nephritis complement damages the basal membrane of the kidney, resulting in the escape of protein from the blood into the urine. The disease disseminated lupus erythematosus belongs in this category; its symptoms include nephritis, visceral lesions and skin eruptions. The treatment of diphtheria or tetanus with the injection of large amounts of antitoxin sometimes results in serum sickness, an immune-complex disease. Rheumatoid arthritis also involves immune complexes. Like disseminated lupus erythematosus, it is an autoimmune disease, in which the disease symptoms are caused by pathological effects of the immune system in the host's tissues. In summary, the complement system has been shown to be involved with inflammation, coagulation, fibrinolysis, antibody-antigen reactions and other metabolic processes.

In the presence of antibody-antigen complexes the complement proteins are involved in a series of reactions which may lead to irreversible membrane damage if they occur in the vicinity of biological membranes. Thus, while complement constitutes a part of the body's defense mechanism against infection, it also results in inflammation and tissue damage in the immunopathological process. The nature of certain of the complement proteins, suggestions regarding the mode of complement binding to biological membranes and the manner in which complement effects membrane damage are discussed in *Annual Review in Biochemistry*, 38, 389 (1969).

It has been reported that the known complement inhibitors epsilon-aminocaproic acid, Suramin Sodium and tranexamic acid all have been used with success in the treatment of hereditary angioneurotic edema, a disease state resulting from an inherited deficiency or lack of function of the serum inhibitor of the activated first component of complement (C1 inhibitor), *The New England Journal of Medicine*, 286, 808-812 (1972); *Allergol. Et. Immunopath*, II, 163-168 (1974); and *J. Allergy Clin. Immunol.*, 53, No. 5, 298-302 (1974); and *Annals of Internal Medicine*, 84, 580-593 (1976).

SUMMARY OF THE INVENTION

It has now been discovered that certain malto-dextrin poly(H-)sulfate salts interact with the complement reaction sequence, thereby inhibiting complement activity in body fluids.

This invention is particularly concerned with a process for preparing poly(H-)sulfate salts of a series of commercially available malto-dextrins sold by American Maize Products Company, under the tradename Fro-Dex®, and with the sulfated products obtained. The malto-dextrin (Fro-Dex®) products are solid forms of corn syrup. They are pure, white carbohydrates composed essentially of dextrose, maltose and high molecular weight saccharides. Further information on the Fro-Dex® malto-dextrins used to prepare the Fro-Dex® malto-dextrin poly(H-)sulfate salts of this invention may be obtained from a brochure by the Technical Service Department, American Maize-Products Company, Hammond, Indiana, entitled "Amaizo Technical Information Amaizo Fro-Dex®", December, 1974, and the contents of this brochure are incorporated herein by reference thereto.

Representative malto-dextrin poly(H-)sulfate salts within the scope of the present invention, include, for example poly(H-)sulfate salts of the above described Fro-Dex® products wherein the salts are selected from alkali metals, alkaline earth metals, ammonium and amines such as trialkylamines ($C_1$-$C_6$), pyrazine, piperidine, alkanolamines ($C_1$-$C_6$); and cycloalkanolamines ($C_3$-$C_6$).

The malto-dextrin poly(H-)sulfate and salts thereof of this invention may be prepared by the application or adaptation of known methods, for example, as descussed in Chemical Reviews, 62: 549–589 (1962); U.S. Pat. Nos. 2,868,779; 2,697,093; 2,923,704 and 3,271,388. They may be produced by sulfating the particular Fro-Dex® malto-dextrin, e.g. Fro-Dex® 10, Fro-Dex® 15, Fro-Dex® 24–924, Fro-Dex® 36, or Fro-Dex® 42, with suitable sulfating agents such as chlorosulfonic acid-pyridine, pyridine-sulfur trioxide, chlorosulfonic acid-formamide, sulfur trioxide in sulfur dioxide, sulfamic acid, sulfur trioxide-aliphatic tertiary amine complexes such as sulfur trioxide-trimethylamine, and sulfur trioxide-ether complexes such as sulfur trioxide-dioxane. The resultant compounds may be converted into the alkali metal or alkaline earth metal salts such as the sodium, potassium, lithium, calcium or barium salts by treating the aforemention sulfates with an alkali metal or alkaline earth metal compound such as sodium acetate, calcium acetate, potassium acetate, etc.

The Fro-Dex® malto-dextrin poly(H-)sulfate salts of the invention may be prepared by dissolving or suspending the Fro-Dex® malto-dextrin in an organic solvent such as dimethylformamide or hexamethyl phosphoramide at 20°-100° C. To this is added the salt forming substituent such as trimethylamine sulfur trioxide or triethylamine sulfur trioxide and the mixture is stirred and heated at 20°-100° C for 8-24 hours. The addition of an organic solvent such as acetone causes the precipitation of the poly(H-)sulfate salt which is collected by conventional methods and may be further purified by reprecipitation from organic solvents such as ether or alcohol. The alkali or alkaline earth metal salts may be prepared by dissolving the above trimethyl- or triethyl-amine salts in water, adding aqueous alkali acetate and charcoal and filtering through diatomaceous earth. The filtrate is poured into ethanol causing precipitation of the poly(H-)sulfate alkali salt. This salt is again dissolved in water, alkali acetate is added and the salt is again precipitated from ethanol.

This invention is also concerned with a method of inhibiting the complement system in a body fluid, such as blood serum, which comprises subjecting body fluid complement to the action of an effective complement inhibiting amount of a poly(H-)sulfate salt of malto-dextrin of this invention. The method of use aspect of this invention is also concerned with a method of inhibiting the complement system in a warm-blooded animal which comprises internally administering to said animal an effective complement inhibiting amount of a poly(H-)sulfate salt of malto-dextrin of this invention. Body fluid can include blood, plasma, serum, synovial fluid, cerebrospinal fluid, or pathological accumulations of fluid as pleural effusion, etc.

The poly(H-)sulfate salts of malto-dextrin of the present invention find utility as complement inhibitors in body fluids and as such may be used to ameliorate or prevent those pathological reactions requiring the function of complement and in the therapeutic treatment of warm-blooded animals having immunologic diseases such as rheumatoid arthritis, systemic lupus erythematosus, certain kinds of glomerulonephritis, certain kinds of auto-allergic hemolytic anemia, certain kinds of platelet disorders and certain kinds of vasculitis. The compounds herein may also be used in the therapeutic treatment of warm-blooded animals having non-immunologic diseases such as paroxysmal nocturnal hemoglobinuria, hereditary angioneurotic edema (treated with Suramin, etc.) and inflammatory states induced by the action of bacterial or lysosomal enzymes on the appropriate complement components as for example, inflammation following coronary occlusion. They may also be useful in the treatment of transplant rejection and as blood culture and transport mediums.

DETAILED DESCRIPTION OF THE INVENTION

The following examples described in detail the preparation and formulation of representative compounds of the present invention.

EXAMPLE 1

Fro-Dex® 10 Poly(H-)sulfate Trimethylamine Salt

A 901 mg portion of Fro-Dex® 10 is suspended in 25 ml of hexamethyl phosphoramide. Water is added dropwise (1.1 ml) with stirring while the mixture is heated in an oil bath at 60°-70° C. A 3.5 g portion of trimethylamine sulfur trioxide is added and the solution is stirred at 60°-70° C for 18 hours. The solution is poured into 100 ml of acetone. The resulting gummy solid is triturated with a second portion of acetone, then with ethanol and finally with ether to give 1.07 g of hygroscopic white powder.

EXAMPLE 2

Fro-Dex® 10 Poly(H-)sulfate Triethylamine Salt

A 0.42 g portion of Fro-Dex® 10 is dissolved in 5 ml of dimethylformamide. A 1.5 g portion of triethylamine sulfur trioxide is added and the mixture is stirred for 18 hours at room temperature. A 50 ml portion of acetone is added. The resulting white flocculent solid is collected and washed with acetone and dried in vacuo at 78° C over phosphorous pentoxide giving 1.34 g. A 500 mg portion of this solid is dissolved in methanol with heat and precipitated with acetone while hot. The mixture is cooled, filtered and the solid is dried at 78° C over phosphorous pentoxide in vacuo giving 276 mg of white solid.

EXAMPLE 3

Fro-Dex® 15 Poly(H-)sulfate Trimethylamine Salt

A 2.50 g portion of trimethylamine sulfur trioxide is dissolved in 30 ml of dimethylformamide at 60°-70° C.

A 900 mg portion of Fro-Dex ® 15 is added and the mixture is stirred for 18 hours at 60°–70° C. A light yellow gum separates and is collected and washed with fresh dimethyl formamide followed by absolute ethanol. The resulting solid is triturated with absolute ethanol and then ether and dried giving 1.96 g of an amorphous white solid.

EXAMPLE 4

Fro-Dex ® 10 Poly(H-)sulfate Sodium Salt

A 2.5 g portion of Fro-Dex ® 10 and 8.6 g of trimethylamine sulfur trioxide are suspended in 60 ml of dimethylformamide and heated with stirring at 60°–70° C for 24 hours. The resulting orange gum is collected and triturated with fresh dimethylformamide and then with absolute ethanol giving a white solid. This solid is collected and dried giving 6.3 g of Fro-Dex ® 10 poly(H-)sulfate trimethylamine salt.

A 6.0 g portion of the above product is dissolved in 10 ml of water and 5 ml of aqueous 30% sodium acetate is added. Charcoal is added and the mixture is filtered through diatomaceous earth. The filtrate is poured into 200 ml of ethanol. The resulting white solid is collected and redissolved in 25 ml of water. A 2.5 ml portion of aqueous 30% sodium acetate is added and the mixture is poured into 200 ml of ethanol. The resulting white solid is collected and dried in vacuo at room temperature over phosphorous pentoxide for 24 hours giving 3.8 g.

EXAMPLE 5

Fro-Dex ® 15 Poly(H-)sulfate Sodium Salt

A 7.5 g portion of trimethylamine sulfur trioxide is dissolved in 75 ml of dimethylformamide. A 2.7 g portion of Fro-Dex ® 15 is added and the mixture is stirred for 20 hours at 60°–70° C. The resulting gum is triturated with dimethylformamide and then with absolute ethanol giving an off-white solid which is washed with absolute ethanol and dried in vacuo giving 6.3 g of Fro-Dex ® 15 poly(H-)sulfate trimethylamine salt.

A 6.0 g portion of the above product is dissolved in 15 ml of water and 7.5 ml of aqueous 30% sodium acetate is added. Charcoal is added and the mixture is filtered three times through diatomaceous earth. The filtrate is poured slowly into 150 ml of absolute ethanol giving a white solid which is collected by filtration. This solid is redissolved in 10 ml of water and 5 ml of aqueous 30% sodium acetate is added. This mixture is filtered twice through diatomaceous earth. The filtrate is poured into 150 ml of ethanol and the resulting solid is collected and dried in vacuo over phosphorous pentoxide at room temperature for 24 hours giving 3.25 g of a white solid.

EXAMPLE 6

Fro-Dex ® 24-924 Poly(H-)sulfate Trimethylamine Salt

A 2.0 g portion of Fro-Dex ® 24-924 is suspended in 40 ml of dimethylformamide and stirred for 30 minutes at 60°–70° C. A 4.0 g portion of trimethylamine sulfur trioxide is added and stirring is continued at 60°–70° C for 18 hours. This mixture is poured into 250 ml of absolute ethanol. The resulting tan solid is collected by filtration, washed with absolute ethanol followed by anhydrous ether and then dried in vacuo at room temperature over phosphorous pentoxide giving 4.16 g of tan solid.

EXAMPLE 7

Fro-Dex ® 36 Poly(H-)sulfate Trimethylamine Salt

A 2.0 g portion of Fro-Dex ® 36 is suspended in 35 ml of dimethylformamide and stirred until solution is complete in an oil bath at 60°–70° C. A 4.0 g portion of trimethylamine sulfur trioxide is added and the mixture is stirred for 18 hours at 60°–70° C. This is poured into 250 ml of absolute ethanol. The resulting white solid is collected by filtration, washed several times with absolute ethanol followed by anhydrous ether and dried in vacuo at room temperature over phosphorous pentoxide giving 4.05 g of white solid.

EXAMPLE 8

Fro-Dex ® 42 Poly(H-)sulfate Trimethylamine Salt

A 2.0 g portion of Fro-Dex ® 42 is suspended in 35 ml of dimethylformamide at 60°–70° C with stirring until solution is complete. A 4.0 g portion of trimethylamine sulfur trioxide is added and stirring is continued for 18 hours at 60°–70° C. This solution is poured into 250 ml of absolute ethanol. A gummy solid separates. The ethanol is decanted and the gum is washed three times with fresh absolute ethanol. The resulting solid is washed once with absolute ether and then dried in vacuo over phosphorous pentoxide at room temperature giving 3.77 g of tan solid.

EXAMPLE 9

Fro-Dex ® 24-924 Poly(H-)sulfate Sodium Salt

A 3.6 g portion of Fro-Dex ® 24-924 poly(H-)sulfate trimethylamine salt is dissolved in 12 ml of water and filtered through diatomaceous earth. A 6 ml portion of aqueous 30% sodium acetate is added and the mixture is poured with stirring into 150 ml of ethanol. The resulting light tan solid is collected by filtration and washed several times with ethanol. This solid is redissolved in 8 ml of water and 4 ml of aqueous 30% sodium acetate is added. The mixture is poured into 150 ml of ethanol with stirring. The resulting off-white solid is washed several times with ethanol and then with ether and dried in vacuo over phosphorous pentoxide for 18 hours at room temperature giving 2.92 g of product.

EXAMPLE 10

Fro-Dex ® 36 Poly(H-)sulfate Sodium Salt

A 3.5 g portion of Fro-Dex ® poly(H-)sulfate trimethylamine salt is dissolved in 10 ml of water and filtered. A 5 ml portion of aqueous 30% sodium acetate is added and the mixture is poured into 150 ml of ethanol with stirring. The resulting white solid is collected by filtration. The solid is dissolved in 10 ml of water, 5 ml of aqueous 30% sodium acetate is added and the mixture is poured into 150 ml of ethanol. The resulting white flocculant precipitate is collected by filtration, washed with ethanol and then with ether and dried in vacuo over phosphorous pentoxide for 8 hours giving 3.1 g of product.

EXAMPLE 11

Fro-Dex ® 42 Poly(H-)sulfate Sodium Salt

A 3.2 g portion of Fro-Dex ® 42 (poly(H-)sulfate trimethylamine salt is dissolved in 10 ml of water and filtered. A 5 ml portion of aqueous 30% sodium acetate is added and the mixture is poured with stirring into 150 ml of ethanol. The resulting white precipitate is collected by filtration. The precipitate is dissolved in 10 ml of water, 5 ml of aqueous 30% sodium acetate is added, and the mixture is poured into 150 ml of ethanol with stirring. The off-white precipitate is collected by filtration, washed three times with ethanol followed by anhydrous ether and then dried in vacuo over phosphorous pentoxide for 8 hours giving 2.7 g of product.

EXAMPLE 12

| Preparation of Compressed Tablet | |
|---|---|
| | mg/tablet |
| Active Component | 0.5–500 |
| Dibasic Calcium Phosphate NF | qs |
| Starch USP | 40 |
| Modified Starch | 10 |
| Magnesium Stearate USP | 1–5 |

EXAMPLE 13

| Preparation of Compressed Tablet-Sustained Action | |
|---|---|
| | mg/tablet |
| Active Component as Aluminum Lake*, Micronized | 0.5–500 as acid equivalent |
| Dibasic Calcium Phosphate NF | qs |
| Alginic Acid | 20 |
| Starch | 35 |
| Magnesium Stearate USP | 1–10 |

EXAMPLE 14

| Preparation of Hard Shell Capsule | |
|---|---|
| | mg/capsule |
| Active Component | 0.5–500 |
| Lactose, Spray Dried | qs |
| Magnesium Stearate | 1–10 |

EXAMPLE 15

| Preparation of Oral Liquid (Syrup) | |
|---|---|
| | % W/V |
| Active Component | 0.05–5 |
| Liquid Sugar | 75.0 |
| Methyl Paraben USP | 0.18 |
| Propyl Paraben USP | 0.02 |
| Flavoring Agent | qs |
| Purified Water qs ad | 100.0 |

EXAMPLE 16

| Preparation of Oral Liquid (Elixir) | |
|---|---|
| | % W/V |
| Active Component | 0.05–5 |
| Alcohol USP | 12.5 |
| Glycerin USP | 45.0 |
| Syrup USP | 20.0 |
| Flavoring Agent | qs |
| Purified Water qs ad | 100.0 |

EXAMPLE 17

| Preparation of Oral Suspension (Syrup) | |
|---|---|
| | % W/V |
| Active Component as Aluminum Lake, Micronized | 0.05–5 (acid equivalent) |
| Polysorbate 80 USP | 0.1 |
| Magnesium Aluminum Silicate, | 0.3 |

-continued

| Preparation of Oral Suspension (Syrup) | |
|---|---|
| | % W/V |
| Colloidal | |
| Flavoring Agent | qs |
| Methyl Paraben USP | 0.18 |
| Propyl Paraben USP | 0.02 |
| Liquid Sugar | 75.0 |
| Purified Water qs ad | 100.0 |

EXAMPLE 18

| Preparation of Injectable Solution | |
|---|---|
| | % W/V |
| Active Component | 0.05–5 |
| Benzyl Alcohol N.F. | 0.9 |
| Water for Injection qs ad | 100.0 |

EXAMPLE 19

| Preparation of Injectable Oil | |
|---|---|
| | % W/V |
| Active Component | 0.05–5 |
| Benzyl Alcohol | 1.5 |
| Sesame Oil qs ad | 100.0 |

EXAMPLE 20

| Preparation of Injectable Depo-Suspension | |
|---|---|
| | % W/V |
| Active Component as Aluminum Lake Micronized | 0.05–5 (acid equivalent) |
| Polysorbate 80 USP | 0.2 |
| Polyethylene Glycol 4000 USP | 3.0 |
| Sodium Chloride USP | 0.8 |
| Benzyl Alcohol N. F. | 0.9 |
| HCl to pH 6–8 | qs |
| Water for Injection qs ad | 100.0 |

EXAMPLE 21

| Intra-Articular Preparation | |
|---|---|
| Active Component | 2–20 mg |
| NaCl (physiological saline) | 0.9% |
| Benzyl Alcohol | 0.9% |
| Sodium carboxymethylcellulose | 1–5% |
| pH adjusted to 5.0–7.5 | |
| Water for Injection qs ad | 100% |

The compounds of this invention may be administered internally, e.g., orally or parenterally, e.g., intra-articularly, to a warm-blooded animal to inhibit complement in the body fluid of the animal, such inhibition being useful in the amelioration or prevention of those reactions dependent upon the function of complement, such as inflammatory process and cell membrane damage induced by antigen-antibody complexes. A range of doses may be employed depending on the mode of administration, the condition being treated and the particular compounds being used. For example, for intravenous or subcutaneous use from about 5 to about 50 mg/kg/day, or every six hours for more rapidly excreted salts, may be used. For intra-articular use for large joints such as the knee, from about 2 to about 20 mg/joint per week may be used, with proportionally smaller doses for smaller joints. The dosage range is to be adjusted to provide optimum therapeutic response in the warm-blooded animal being treated. In general, the amount of compound administered can vary over a wide range to provide from about 5 mg/kg to about 100 mg/kg of body weight of animal per day. The usual daily dosage for a 70 kg subject may vary from about 350 mg to about 3.5 g. Unit doses of the salt can contain from about 0.5 mg to about 500 mg.

In therapeutic use the compounds of this invention may be administered in the form of conventional pharmaceutical compositions. Such compositions may be formulated so as to be suitable for oral or parenteral administration. The active ingredient may be combined in admixture with a pharmaceutically acceptable carrier, which carrier may take a wide variety of forms depending on the form of preparation desired for administration, i.e. oral or parenteral. The compounds can be used in compositions such as tablets. Here, the principal active ingredient is mixed with conventional tabletting ingredients such as corn starch, lactose, sucrose, sorbitol, talc, stearic acid, magnesium stearate, dicalcium phosphate, gums, or similar materials as non-toxic pharmaceutically acceptable diluents or carriers. The tablets or pills of the novel compositions can be laminated or otherwise compounded to provide a dosage form affording the advantage of prolonged or delayed action or predetermined successive action of the enclosed medication. For example, the tablet or pill can comprise an inner dosage and outer dosage components, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate and the like. A particularly advantageous enteric coating comprises a styrene maleic acid copolymer together with known materials contributing to the enteric properties of the coating. The tablet or pill may be colored through the use of an appropriate non-toxic dye, so as to provide a pleasing appearance.

The liquid forms in which the novel compositions of the present invention may be incorporated for administration include suitable flavored emulsions with edible oils, such as, cottonseed oil, sesame oil, coconut oil, peanut oil, and the like, as well as elixirs and similar pharmaceutical vehicles. Sterile suspensions or solutions can be prepared for parenteral use. Isotonic preparations containing suitable preservatives are also desirable for injection use.

The term dosage form as described herein refers to physically discrete units suitable as unitary dosage for warm-blooded animal subjects, each unit containing a predetermined quantity of active component calculated to produce the desired therapeutic effect in association with the required pharmaceutical diluent, carrier or vehicle. The specification for the novel dosage forms of this invention are indicated by characteristics of the active component and the particular therapeutic effect to be achieved or the limitations inherent in the art of compounding such an active component for therapeutic use in warm-blooded animals as disclosed in this specification. Examples of suitable oral dosage forms in accord with this invention are tablets, capsules, pills, powder packets, granules, wafers, cachets, teaspoonfuls, dropperfuls, ampules, vials, segregated multiples of any of the foregoing and other forms as herein described.

The complement inhibiting activity of the compounds of this invention has been demonstrated by one or more of the following identified tests: (i) Test, Code 026 (C1 inhibitor)—This test measures the ability of activated human C1 to destroy fluid phase human C2 in the presence of C4 and appropriate dilutions of the test compound. An active inhibitor protects C2 from C1 and C4; (ii) Test, Code 035 (C3–C9 inhibitor)—This test determines the ability of the late components of human complement (C3–C9) to lyse EAC 142 in the presence of appropriate dilutions of the test compound. An active inhibitor protects EAC 142 from lysis by human C3–C9; (iii) Test, Code 036 (C-Shunt inhibitor)—In this test human erythrocytes rendered fragile are lysed in autologous serum via the shunt pathway activated by cobra venom factor in the presence of appropriate dilutions of the test compound. Inhibition of the shunt pathway results in failure of lysis; (iv) Forssman Vasculitis Test—Here, the well known complement dependent lesion, Forssman vasculitis, is produced in guinea pigs by intradermal injection of rabbit anti-Forssman antiserum. The lesion is measured in terms of diameter, edema and hemorrhage and the extent to which a combined index of these is inhibited by prior intraperitoneal injection of the test compound at 200 mg/kg in then reported, unless otherwise stated; (v) Forssman Shock Test—Lethal shock is produced in guinea pigs by an i.v. injection of anti-Forssman antiserum and the harmonic mean death time of treated guinea pigs is compared with that of simultaneous controls; (vi) Complement Level Reduction Test—In this test, the above dosed guinea pigs, or others, are bled for serum and the complement level is determined in undiluted serum by the capillary tube method of U.S. Pat. No. 3,876,376 and compared to undosed control guinea pigs; and (vii) Cap 50 Test—Here, appropriate amounts of the test compound are added to a pool of guinea pig serum in vitro, after which the undiluted serum capillary tube assay referred to above is run. The concentration of compound inhibiting 50% is reported.

The compounds of the present invention have been found to possess anti-coagulant activity as well as complement inhibiting activity. The in vitro anti-coagulant activity (AC) of the compounds of this invention has been demonstrated by the following test: Citrated sheep plasma (CSP) is added to various dilutions of test compound in Microtiter ® plate, CSP sample mixtures are then recalcified with an isotonic sheep red blood cell (RBC) suspension. The sheep RBC's, kept in suspension throughout the clotting incubation time, become enmeshed in the fibrin matrix if a clot forms. Upon centrifugation of the plate untrapped RBC's form buttons, the sizes of which correspond to the degree of clot inhibition; thus providing a measure of anti-coagulant activity (AC). Sodium heparin is used as a positive control and activity is reported in wells appearing in Table I.

With reference to Table I, guinea pigs weighing about 300 g were dosed intravenously (i.v.) or intraperitoneally, (i.p.) with the indicated amount of the test compound dissolved in saline and adjusted to pH 7–8. One hour after dosing, the guinea pigs were decapitated, blood was collected and the serum separated. The serum was tested for whole complement using the capillary tube assay. Percent inhibition was calculated by comparison with simultaneous controls. The results appear in Table I together with results of tests, code 026, 035, 036, Cap 50, % inhibition and Forssman shock. Table I shows that the compounds of the invention possess complement inhibiting activity.

ration of activities. The *Intrinsic Therapeutic Index* of the compounds of this invention are listed in Table II.

TABLE II

| | INTRINSIC THERAPEUTIC INDEX | | | |
|---|---|---|---|---|
| | IN VITRO ACTIVITY | | | |
| COMPOUND | Complement Inhibiting Activity (Wells) Code 026 | Anti-Coagulant Activity (Wells) AC | Logarithmic Difference Expressed as Wells | INTRINSIC THERAPEUTIC INDEX |
| FRO-DEX® 10 Poly(H—)sulfate Trimethylamine salt | +10 | +3 | +7 | 128 |
| FRO-DEX® 10 Poly(H—)sulfate trimethylamine salt | +8 | +2 | +6 | 64 |
| FRO-DEX® 10 Poly(H—)sulfate sodium salt | +9 | +4 | +5 | 32 |
| FRO-DEX® 15 Poly(H—)sulfate trimethylamine salt | +10 | +2 | +8 | 256 |
| FRO-DEX® 15 Poly(H—)sulfate sodium salt | +10 | +5 | +5 | 32 |
| FRO-DEX® 24–924 Poly(H—)sulfate trimethylamine salt | +8 | +1 | +7 | 128 |
| FRO-DEX® 24–924 Poly(H—)sulfate sodium salt | +8 | +2 | +6 | 64 |
| FRO-DEX® 36 Poly(H—)sulfate trimethylamine salt | +9 | +1 | +8 | 256 |
| FRO-DEX® 36 Poly(H—)sulfate sodium salt | +8 | +2 | +6 | 64 |
| FRO-DEX® 42 Poly(H—)sulfate trimethylamine salt | +8 | +1 | +7 | 128 |
| FRO-DEX® 42 Poly(H—)sulfate sodium salt | +9 | +2 | +7 | 128 |

TABLE I

| | BIOLOGICAL ACTIVITIES | | | | | | | | | | |
|---|---|---|---|---|---|---|---|---|---|---|---|
| | IN VIVRO ACTIVITY | | | | | | IN VIVO Activity (Guinea Pig) % Inhibition | | | | |
| | | | | | | | Intraperitoneal Time (Hours) | | | Intravenous Time (Hours) | |
| | 026* | 035* | 036* | AC* | CAP | Dose | | | | | |
| Compound | Wells | Wells | Wells | Wells | 50* | (MG/KG) | 30 | 60 | 120 | 2 | 2 | 120 |
| FRO-EEX® 10 Poly(H—)sulfate trimethylamine salt | +10 | +4 | +4 | +3 | 81 | | | | | | | |
| FRO-DEX® 10 Poly(H—)sulfate triethylamine salt | +8 | +4 | +4 | +2 | 113 | | | | | | | |
| FRO-DEX® 10 Poly(H—)sulfate sodium slat | +10 | +4 | +4 | +4 | 79 | 200 | −63 | −93 | −98 | −98 | 99 | |
| | +8 | +3 | | | 77 | 100 | | | | −99 | | |
| | | | | | | 50 | | | | −99 | −98 | −88 |
| | | | | | | 25 | | | | −98 | −79 | −33 |
| | | | | | | 12.5 | | | | | | |
| FRO-DEX® 15 Poly(H—)sulfate trimethylamine salt | +9 | +4 | +4 | +2 | 170 | | | | | | | |
| | +11 | | | | 141 | | | | | | | |
| FRO-DEX® 15 Poly(H—)sulfate sodium salt | +11 | +4 | +4 | +5 | 121 | 200 | −52 | −88 | −98 | −98 | −99 | −99 |
| | +8 | | | | | 100 | | | | −99 | −98 | −76 |
| | | | | | | 50 | | | | −99 | −97 | −82 |
| | | | | | | 25 | | | | | | |
| FRO-DEX® 24–924 Poly(H—)sulfate trimethylamine salt | +8 | +2 | +4 | +1 | 166 | | | | | | | |
| FRO-DEX® 24–924 Poly(H—)sulfate sodium salt | +8 | +2 | +5 | +2 | 163 | 200 | −34 | −12 | −78 | −97 | −97 | −72 |
| | | | | | | 100 | | | | | | |
| FRO-DEX® 36 Poly(H—)sulfate trimethylamine salt | +9 | +1 | +4 | +1 | 483 | | | | | | | |
| FRO-DEX® 36 Poly(H—)sulfate sodium salt | +8 | +1 | +5 | +2 | 326 | 200 | −20 | −14 | −35 | −72 | −30 | −21 |
| | | | | | | 100 | | | | | | |
| FRO-DEX® 42 Poly(H—)sulfate trimethylamine salt | +8 | +1 | +5 | +1 | 290 | | | | | | | |
| FRO-DEX® 42 Poly(H—)sulfate sodium salt | +9 | +1 | +5 | +2 | 293 | 200 | 0 | +6 | +30 | −89 | −64 | −57 |
| | | | | | | 100 | | | | | | |

*Code designation for tests employed as referred to herein
**Activity in wells, a serial dilution assay. Higher well number indicates higher activity. The serial dilutions are two-fold.

The computation of an *Intrinsic Therapeutic Index* (ITI) was devised to correlate the results expressed in wells, obtained in the in vitro code 026 (C1 inhibitor) test and the in vitro anti-coagulant (AC) test into a meaningful value which would aid in the net evaluation of the activity of the compounds of this invention. The ITI of a given compound may be defined as the antilogarithm of the logarithmic (base 2) difference between the highest serial dilution in wells which is active in the code 026 test and the highest serial dilution in wells providing activity in the anti-coagulant test. The ITI is thus a measure of the separation of anti-complement and anti-coagulant activities; the higher the numerical value the more therapeutically useful the sepa-

We claim:

1. A Fro-Dex® malto-dextrin poly(H-)sulfate and salt thereof prepared by sulfating a Fro-Dex® malto-dextrin in the presence of a member selected from the group comprising alkali metal, alkaline earth metal, trialkylamine ($C_1$–$C_6$), alkanolamine ($C_1$–$C_6$), cycloalkanolamine ($C_3$–$C_6$), pyrazine and piperidine.

2. A compound Fro-Dex® 10 poly(H-)sulfate trimethylamine salt according to claim 1.

3. A compound Fro-Dex® 10 poly(H-)sulfate triethylamine salt, according to claim 1.

4. A compound Fro-Dex® 15 poly(H-)sulfate trimethylamine salt, according to claim 1.

5. A compound Fro-Dex ® 10 poly(H-)sulfate sodium salt, according to claim 1.

6. A compound Fro-Dex ® 15 poly(H-)sulfate sodium salt, according to claim 1.

7. A compound Fro-Dex ® 24-924 poly(H-)sulfate trimethylamine salt, according to claim 1.

8. A compound Fro-Dex ® 36 poly(H-)sulfate trimethylamine salt, according to claim 1.

9. A compound Fro-Dex ® 42 poly(H-)sulfate trimethylamine salt, according to claim 1.

10. A compound Fro-Dex ® 24-924 poly(H-)sulfate sodium salt, according to claim 1.

11. A compound Fro-Dex ® 36 poly(H-)sulfate sodium salt, according to claim 1.

12. A compound Fro-Dex ® 42 poly(H-)sulfate sodium salt, according to claim 1.

* * * * *